United States Patent [19]

Rubin

[11] Patent Number: 5,741,970
[45] Date of Patent: Apr. 21, 1998

[54] IMPACT MEASURING APPARATUS

[76] Inventor: Martin D. Rubin, 11 Wharton Ct., Kendall Park, N.J. 08824

[21] Appl. No.: 410,323

[22] Filed: Mar. 24, 1995

[51] Int. Cl.⁶ .............. A63B 69/00; G01L 5/02; A61B 5/22
[52] U.S. Cl. ............... 73/379.05; 73/12.01
[58] Field of Search .................. 73/11.01, 12.01, 73/12.07, 12.08, 12.09, 714, 379.04, 379.05, 379.08, 379.09

[56] References Cited

U.S. PATENT DOCUMENTS

| 2,390,336 | 12/1945 | Spearman | 73/379.04 |
|---|---|---|---|
| 2,680,967 | 6/1954 | Newman . | |
| 2,767,920 | 10/1956 | Roberson . | |
| 3,365,947 | 1/1968 | Janich, III et al. . | |
| 3,380,305 | 4/1968 | Charell | 73/379.04 |
| 4,027,875 | 6/1977 | Hurley . | |
| 4,088,315 | 5/1978 | Schemmel . | |
| 4,108,428 | 8/1978 | Winterbottom . | |
| 4,534,557 | 8/1985 | Bigelow et al. | 73/379.04 |
| 4,565,366 | 1/1986 | Struss . | |
| 4,824,107 | 4/1989 | French . | |
| 4,850,224 | 7/1989 | Timme . | |
| 4,883,271 | 11/1989 | French . | |
| 4,941,660 | 7/1990 | Winn et al. . | |
| 5,551,280 | 9/1996 | Lee | 73/12.09 |

FOREIGN PATENT DOCUMENTS

| 2708072 | 8/1978 | Germany | 73/379.04 |
|---|---|---|---|
| 2717104 | 10/1978 | Germany | 73/379.04 |

Primary Examiner—George M. Dombroske
Attorney, Agent, or Firm—Plevy & Associates

[57] ABSTRACT

An apparatus for measuring the force of an impact delivered by a user, comprises an impact receiving section for absorbing the impacts delivered by the user. The impact receiving section includes an open cell foam layer for generating pressure pulses which vary in amplitude according to the location where the impact is delivered on the impact receiving section by the user. A pressure sensor which communicates with the impact receiving section, is provided for receiving the pressure pulses generated by the open cell foam layer and provides an electrical signal which is indicative of the impacts delivered by the user. The apparatus also includes an electrical circuit which comprises a high pass filter coupled to the pressure sensor, for filtering the electrical signal generated by the pressure sensor. A threshold detector circuit is coupled to the high pass filter, for detecting if the electrical signal exceeds a predetermined level. The threshold detector is also coupled to a reflex tester circuit for measuring the user's reflexes. A peak detector and storage circuit responsive to the threshold detector circuit, is coupled to the high pass filter, for tracking the peak level of any electrical signal exceeding the predetermined level and storing that peak level. A display circuit is coupled to the peak detector/storage circuit and the reflex tester circuit for displaying the stored peak level to the user as a measure of force and the response time of the user's reflexes.

12 Claims, 9 Drawing Sheets

FIG. 5

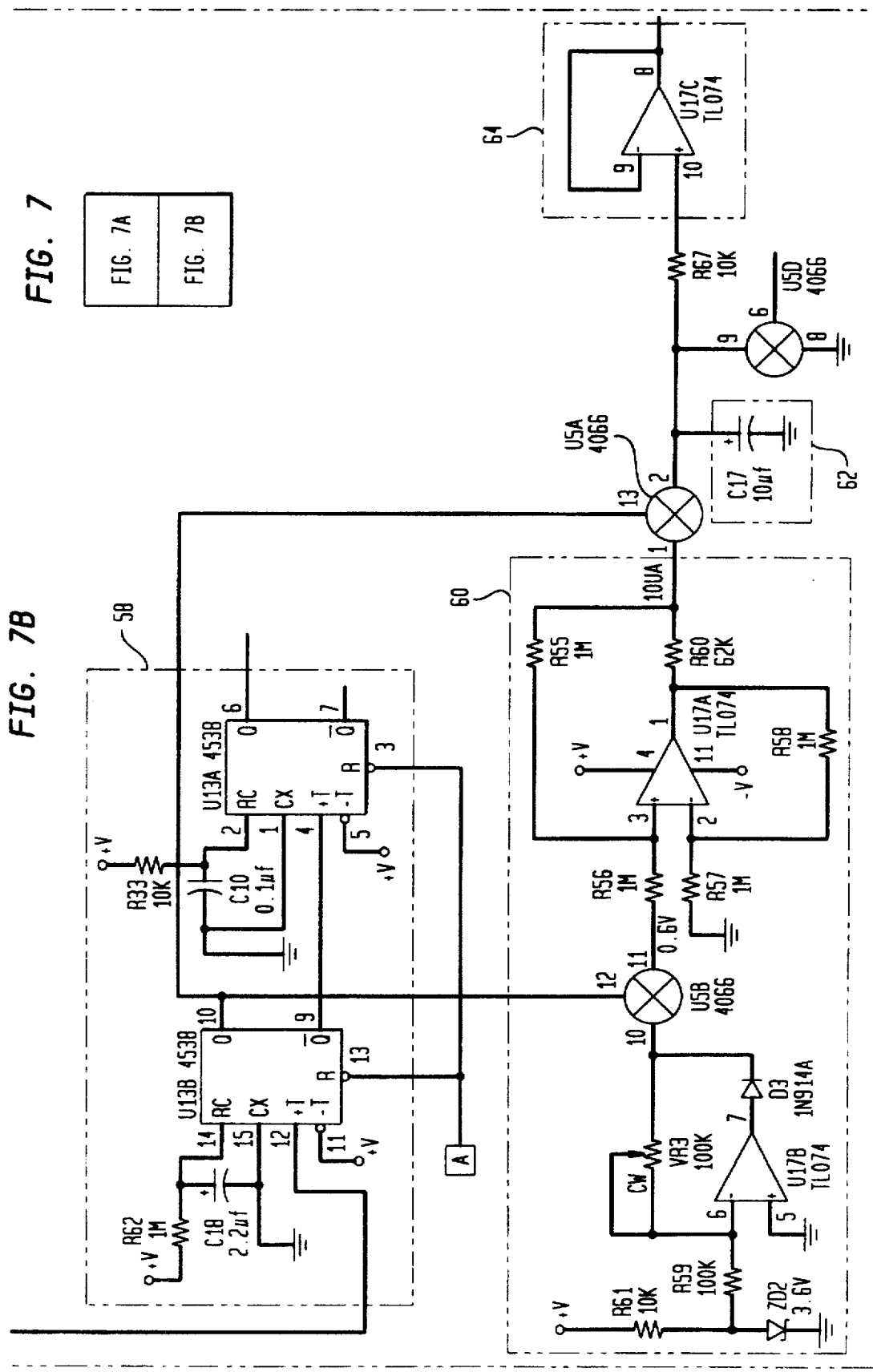

IMPACT MEASURING APPARATUS

FIELD OF THE INVENTION

This invention relates generally to an impact measuring apparatus and more particularly to an improved apparatus for providing a force measurement which is dependent upon the location or accuracy of a punch or kick delivered to the apparatus by a user. The improved apparatus further provides a measurement of the time it takes for the user to respond to an indicator signal and impact the apparatus.

BACKGROUND OF THE INVENTION

Devices for measuring the force of the impact are well known in the art. Such devices include athletic training apparatus that are designed to be struck by an athletes hands or feet. These athletic training devices are typically adapted to provide the user with an indication of the impact force of his or her punches and kicks thereby providing the athlete with feedback on his or her performance. Accordingly, the feedback enables the user to improve his or her technique and performance.

An apparatus for measuring impact force is described in U.S. Pat. No. 4,850,224 entitled IMPACT APPARATUS issued to Timme on Jul. 25, 1989. The impact measuring device described in the Timme patent employs an impact receiving pad. The impact receiving pad comprises a hollow thin body of high impact polyethylene or equivalent plastic which is lined on its interior surface with a polyurethane foam or an equivalent material. The polyurethane foam is adapted to be more resilient than the material used for fabricating the hollow body. The outer surface of the hollow body is lined with a polyethylene foam or like material. The hollow body also defines an air chamber which communicates with a force indicating apparatus via a conduit. Thus, when the pad is struck air is expelled from the chamber through the conduit to the indicating apparatus which provides an indication of force. The force indicating apparatus disclosed in the Timme patent consist of a rotary disk with a plurality of veins. When the expelled air makes contact with the veins on the disks, the disk rotates and the number of rotations of the disk is counted optoelectrically. The signal created by this arrangement indicates the force of impact.

Another device for providing an athlete with feedback concerning impact force is shown in U.S. Pat. No. 4,941,660 entitled IMPACT AND SPEED MEASURING SYSTEM issued to Winn et al. on Jul. 17, 1990. The Winn et al. patent discloses a foam punching bag that includes a bladder for holding water. The cover of the bladder mounts a pressure transducer. The pressure transducer is coupled to a locally mounted electronic high speed pressure indicator. When the bag is struck by the athlete, an increase in water pressure in the bladder is created and sensed by the pressure transducer. A pressure indicator coupled to the transducer receives a signal from the transducer which is indicative of the increase in water pressure and converts this signal into a reading of force.

Other examples of devices which measure impact force via air pressure generated in some type of punching bag-like apparatus are described in U.S. Pat. No. 2,680,967 entitled APPARATUS FOR MEASURING MUSCLE STRENGTH issued to Newman on Jun. 15, 1954 and in U.S. Pat. No. 4,108,428 entitled PORTABLE PUNCH POWER GAUGE issued to Winterbottom on Aug. 22, 1978.

Some impact force measuring devices are adapted to be worn on the athlete's hands. For example, in U.S. Pat. No. 2,767,920 entitled REGISTERING BOXING GLOVE issued to Roberson on Oct. 23, 1986 describes a boxing glove which includes an integrally formed bladder filled with air. The bladder is coupled to a counter that counts the number of punches that effectively hits a target.

A device which registers the force of blows delivered to a target regardless of the particular location of the blow on the target is disclosed in U.S. Pat. No. 4,565,366 entitled MARTIAL ARTS PRACTICE DEVICE issued to Struss on Jan. 21, 1986. This punching device includes a series of electrical switches which operate to register the force of the blows delivered to the device.

U.S. Pat. No. 4,088,315 entitled DEVICE FOR SELF-DEFENSE TRAINING issued to Schemmel on May 9, 1978 describes a training dummy having a plurality of separate pressure receptors disposed at various target locations on the dummy for measuring the impact forces of blows made to the various locations.

A device for measuring the time it takes for a person to activate a timer on a one switch box and stop the timer by touching a plunger on the other switch box is described in U.S. Pat. No. 4,027,875 entitled REACTION SPEED TRAINING DEVICE issued to Hurley on Jun. 7, 1977.

Impact measuring devices which comprise piezoelectric films mounted on deformable materials are disclosed in U.S. Pat. No. 4,824,107 entitled SPORTS SCORING DEVICE INCLUDING A PIEZOELECTRIC TRANSDUCER issued to French on Apr. 25, 1989 and U.S. Pat. No. 4,883,271 entitled SPORTS IMPACT MEASURING DEVICE issued also to French on Nov. 28, 1989.

Thus, it is apparent from the above list of patents that many different devices have been developed over the years for measuring the force of punches and kicks. Of these prior art devices, many of them are not capable of providing accurate measurements of force. Further, many of these devices are not capable of measuring impacts given in rapid succession.

Other problems associated with most of these prior art devices also exist. For instance, many of these prior art devices are not very durable as they are easily damaged. Moreover, most of these devices are too expensive to be produced or purchased by the general public.

Finally, none of these devices have been successful in providing a force measurement response which is dependent upon the location or accuracy of the punch or kick delivered by the user.

It is therefore a primary object of the present invention to provide an impact apparatus for measuring the force of a punch or kick delivered thereto that provides a location dependent response, a rapid response time, and a rapid recovery time.

It is a further object of the present invention to provide an affordable and robust impact apparatus that measures and displays the force of impact.

It is a still further object of the present invention to provide an impact apparatus that can be used in a variety of applications.

It is a still another object of the present invention to provide an impact apparatus that can provide a measurement of the time it takes for the user to respond to an indicator signal and impact the apparatus.

SUMMARY OF THE INVENTION

An apparatus for measuring the force of an impact delivered by a user and for measuring the user's reflexes, comprises impact receiving means for absorbing the impacts delivered by the user. The impact receiving means includes means for generating pressure pulses which vary in amplitude according to the force of impact and the location where the impact is delivered on the impact receiving means by the user. Signaling means which communicate with the impact receiving means are provided for receiving the pressure pulses generated by the impact receiving means and providing an electrical signal which is indicative of the impacts delivered by the user.

The apparatus also includes electrical signal processing means which comprise high pass filter means coupled to the signaling means, for filtering the electrical signal. Detector means are coupled to the high pass filter means, for detecting if the electrical signal exceeds a predetermined level. The detector means are also coupled to reflex testing means for measuring the user's reflexes. Track/storage means responsive to the detector means, are coupled to the high pass filter means, for tracking the peak level of an electrical signal exceeding the predetermined level and storing that peak level. Display means are coupled to the track/storage means for displaying the peak level to the user as a measure of force. The display means are also coupled to the reflex tester means for displaying the response time of the user's reflexes.

BRIEF DESCRIPTION OF THE DRAWINGS

The above and other features and aspects of the present invention will become more apparent upon reading the following detail description in conjunction with the accompanying drawings, in which.

DETAILED DESCRIPTION

Figure 1:
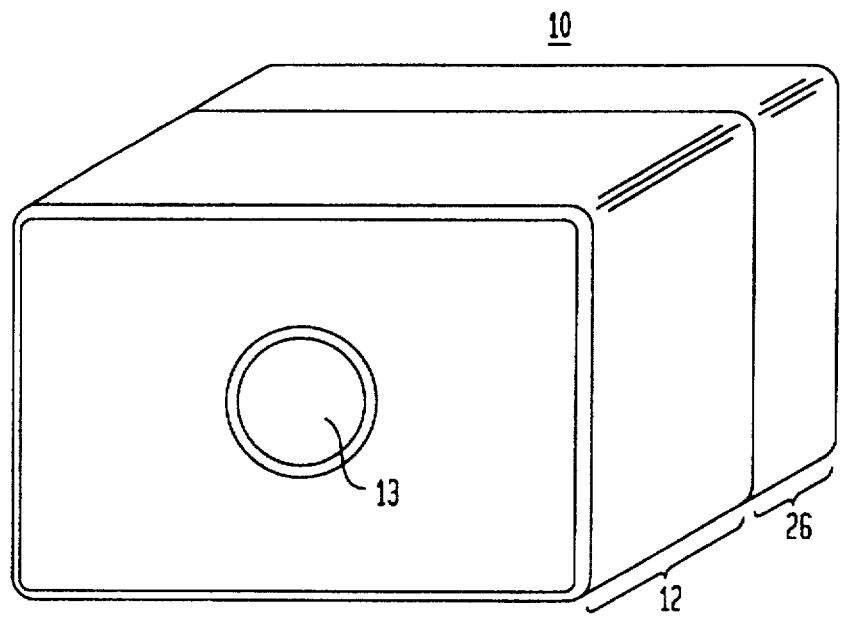
FIG. 1 shows a front perspective view of a preferred exemplary embodiment of the impact measuring apparatus of the present invention.

A front perspective view of a preferred exemplary embodiment of the impact measuring apparatus 10 of the present invention is shown in FIG. 1. The impact measuring apparatus 10 generally comprises a front or impact receiving section 12 and a rear or electronics housing section 26 for enclosing the electronics of the device. The impact receiving section 12 includes a centrally located target area indicia 13 which the user employs to aim his or her punches and kicks at when using the apparatus. In the preferred embodiment shown in FIG. 1, the apparatus 10 is constructed as a rectangular member, although the apparatus 10 can be configured in any other desirable shape. For example, it is contemplated that the present invention can be configured like a conventional "punching bag" which has a tear drop shape, or as a "heavy bag" which is cylindrical in shape.

The general configuration of the impact measuring apparatus 10 shown in FIG. 1 enables it to be positioned on any flat surface such as a wall or floor. If it is desirable for the apparatus 10 to be mounted on a wall, the rear 26 of the apparatus 10 can include any well known wall fastening means such as hooks (not shown) and the like to facilitate such mounting. Such fastening means can also be used to secure the apparatus 10 to a floor or a table.

The rear 26 of the impact apparatus 10 can also include means for mounting the apparatus 10 on a fixed or movable support stand (not shown) or include means for allowing another person to hold the apparatus.

The impact receiving section 12 of the present invention generally comprises one or more layers of resilient material having an open cell configuration. In the preferred embodiment shown in FIG. 2, the impact receiving section 12 comprises a pressure pulse generating layer 16 of resilient material characterized by a randomly oriented open cell configuration. The pressure pulse generating layer 16 is preferably fabricated from polyurethane foam. However, any other suitable material having an open cell configuration can be used such as stiff fibrous filtering material.

Figure 2:
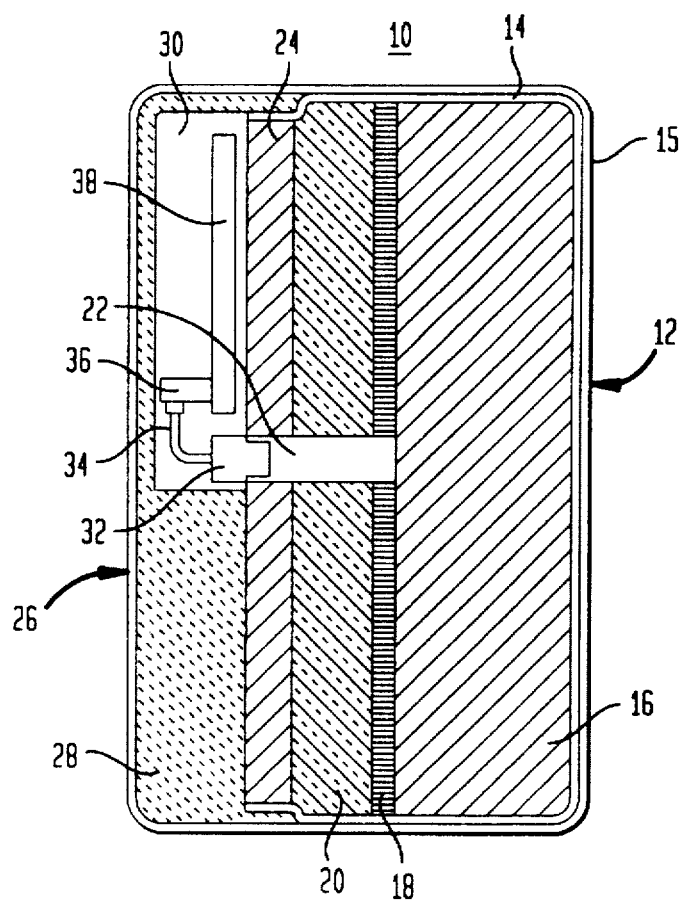
FIG. 2 shows a side cross-sectional view of the impact measuring apparatus of the present invention shown in FIG. 1.

In the preferred embodiment shown in FIG. 2, the pressure pulse generation layer 16 is backed immediately by a pressure pulse guiding layer 18 of fibrous material. The preferred material for the pressure pulse guiding layer 18 comprises a stiff polyester fibrous filtering material. Alternatively, a resilient material having an open cell configuration where the cells are oriented substantially perpendicular to the surface of the pressure pulse generation layer 16 can be employed. This would be desirable in applications where less sensitivity outside of the target area is required.

The pressure pulse guiding layer 18 is backed immediately by a protective layer 20 of resilient material having a closed cell configuration. The protective layer 20 is preferably fabricated from blended sponge rubber or any other suitable material.

The protective layer 20 of the impact receiving section is backed immediately by a rigid solid member 24. In the preferred embodiment, the solid member 24 is fabricated from wood or plastic, although a metal or other rigid shatter-resistant material could be implemented.

The pressure pulse generating layer 16, the pressure pulse guiding layer 18, the protective layer 20, and the solid member 24 are enclosed by an elastic, non-porous layer 14. The non-porous layer 14 is preferably fabricated from a rubber material although any other suitable elastic non-porous material can be employed.

The non-porous layer 14 is coupled to the solid member 24 using any well known method such as by stapling or the like. Such a coupling can be accomplished so that no significant amount of air can escape from the resilient layers or enter the resilient layers during use of the apparatus. This type of "sealed" arrangement, however, is subject to eventual failure thereby destroying the calibrated response of the apparatus. Therefore, in the preferred embodiment, the non-porous layer 14 is coupled to the solid member 24 in a partially sealed manner so that a small amount of air can escape the resilient layers and enter the resilient layers during the use of the apparatus. This enables the apparatus to maintain a much longer period of calibration.

The apparatus 10 is covered by an outer covering 15 made preferably of vinyl or any other suitable material. The outer covering 15 operates to enhance the appearance and protect the apparatus 10. The target area 13 is identified on the outer surface of the outer covering 15 by some type of indicia such as a silk-screened on circle or the like.

The protective layer 20, the solid member 24, and the pressure pulse guiding layer 18 define a centrally located port 22. The port 22 extends perpendicularly from the surface of the pressure pulse generating layer 16 so that the axis of the port 22 extends in the same direction as the axis of the strike and the resulting pressure pulse. The earlier mentioned target area 13 is oriented on the outer covering 15 in a position which is in-line with the port 22.

Still referring to FIG. 2, the electronics housing section 26 comprises a layer of resilient material 28 which is secured to the solid member 24 on the side opposite to the impact receiving section 12. The layer of resilient material 28 is preferably fabricated from any type of suitable foam-like material that is capable of cushioning the user from the solid member 24 and other hard components of the apparatus.

As can be seen, the upper section of the layer of resilient material 28 defines a chamber or space 30. The space 30 is sized to communicate with the port 22. Mounted in the port 22 inside space 28 is a fitting 32 which communicates with a pressure sensor 36 via a hose or tube 34 also positioned within space 30. The hose 34 is coupled at one end to the fitting 32 and at the other end to the pressure sensor 36. In the preferred embodiment, the fitting is adapted to be threaded into the solid member 24 although, any other like arrangement is possible.

Placement of the fitting 32 on the solid member 24 enables the layers of resilient material and the solid member 24 to cushion the fitting 32 from direct impact and substantially prevents the user from striking it and harming him or herself.

The pressure sensor 36 is preferably of the piezoelectric type. Such sensors are readily available from companies like Honeywell which for example, markets a line of piezoelectric pressure sensors known as the 24PC family. The pressure sensor 36 may also be of the semiconductor type if desired.

The pressure sensor 36 is coupled to an electrical circuit 38 which is housed within space 30. The electrical circuit 38 will be described in greater detail later on.

Figure 3A:
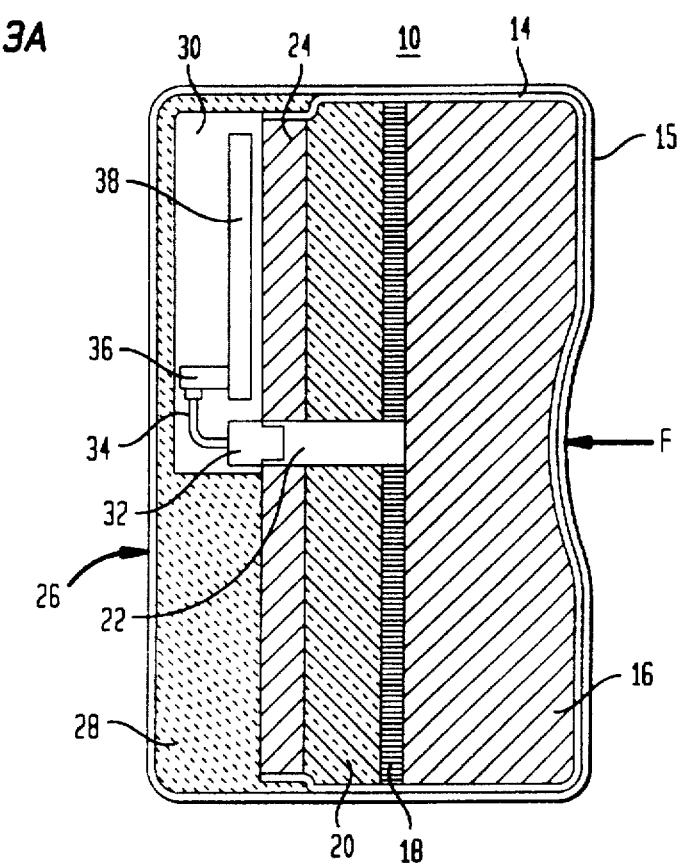
FIG. 3A depicts the impact measuring apparatus of FIG. 2 when a punch or kick is delivered to the target area.

Referring to FIG. 3A, when the user delivers a punch or kick of a given force F to the target area 13 of the impact receiving section 12, air contained within the open cells of the pressure pulse generating layer 16 is suddenly compressed. This is caused by the cells of the first layer distorting from the impact of the punch or kick and generates an air pressure pulse having a given amplitude.

Since the target area 13 is in-line with the port 22, the air pressure pulse wave generated in the pressure pulse generating layer 16 enters the port 22 unattenuated. The pressure pulse wave propagates through the port 22 into the fitting 32. The pressure pulse wave travels through the hose 34 and is sensed by the pressure sensor 36.

The pressure sensor 36 sends an electrical signal, in response to the sensed pressure pulse wave, to the electrical circuit 38 which processes the signal into a measurement of the given force. The measurement is then visually or audibly displayed or indicated, as will be explained later below.

The present invention is also capable of providing a location dependent response for indicating when and how far outside of the target area a punch or kick delivered by the user is. The operation of the apparatus under such a condition will now be described in conjunction with FIG. 3B.

Figure 3B:
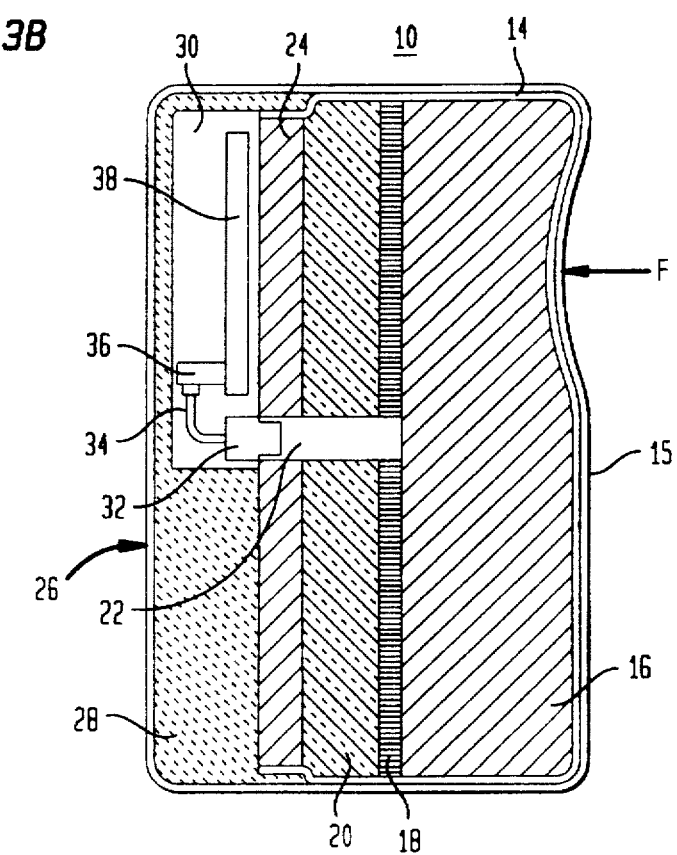
FIG. 3B depicts the impact measuring apparatus of FIG. 2 when a punch or kick is delivered to an area outside of the target area.

In FIG. 3B, the user has delivered a punch or kick of a given force F to a location outside of the target area 13 of the impact receiving section 12 which generates an air pressure pulse.

Since the air pressure pulse wave is generated in a section of the pressure pulse generating layer 16 that is above the port 22, the wave must travel down through the pressure pulse generating layer 16 and the pressure pulse guiding layer 18 in order to reach the port 22. The closed cell construction of the protective layer 20 aids in guiding the pressure pulse to the port 22 because the closed cell construction reflects the pressure pulse down through the pressure guiding layer 18. As the wave travels through the randomly oriented arrangement of open cells in the pressure pulse generating layer 16 and the fibrous structure of the pressure pulse guiding layer 18, the amplitude of the pressure pulse wave becomes attenuated. The amplitude of the pressure pulse wave 40 becomes attenuated an amount proportionate to the distance away from the target area 13. The attenuated pressure pulse wave 40 propagates through the port 22, the fitting 32, and the hose 34 and is sensed by the pressure sensor 36 as earlier described.

The pressure sensor 36 then sends an electrical signal indicative of the attenuated pressure pulse 40 to the electrical circuit 38 to be processed and displayed as an attenuated measurement of the given force. The reduced indication of force tells the user that the punch or kick was not in the target area. Moreover, the user will also be able to recognize how far outside the target area the punch or kick was as a lower indicated force measurement will be displayed as the punches and kicks move farther outside the target area.

Figure 4:
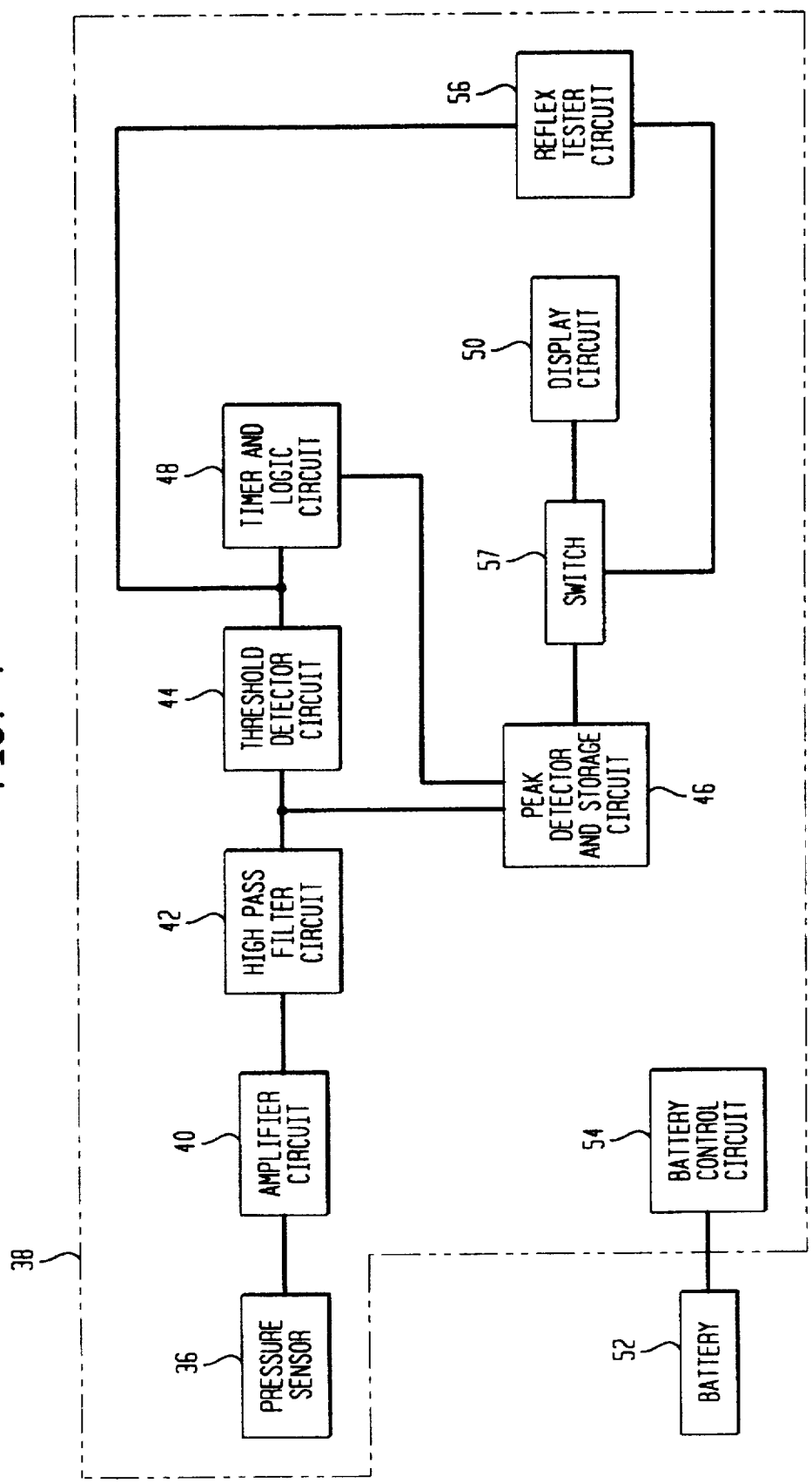
FIG. 4 is a block diagram of the electrical circuit of the present invention.

Referring to FIG. 4, there is shown a block diagram of the electrical circuit 38 which is coupled to the pressure sensor 36 of the present invention.

The pressure sensor 36 shown in FIG. 4 can be a piezoelectric device, such as a Honeywell 24PC family. Other similar devices that are capable of converting a pressure pulse into an electrical signal can be utilized. The electrical signal generated by the pressure sensor 36 is applied to an amplifier circuit 40. The amplifier circuit 40 can utilize an operational amplifier, such as a National TL074.

The amplified signal generate by the amplifier circuit 40 is applied to a high pass filter circuit 42. The high pass filter circuit 42 can comprise a first order resistor/capacitor design which may include an operational amplifier, such as a National TL074, as a voltage follower. The high pass filter circuit 42 attenuates any low frequency signal that may received. One example of such a low frequency signal can be generated by the pressure sensor 36 when a gradual application of pressure is received by the impact receiving section 12 of impact measuring apparatus 10. Another example of such a signal includes a DC signal generated by the pressure sensor 36 when a steady pressure is applied to the impact receiving section 12 of the impact apparatus 10. In any event, it is important to isolate these signals in order to more accurately measure the impact force.

The high frequency signals which pass through the high pass filter circuit 42 are applied to a threshold detector circuit 44 and a peak detector and storage circuit 46. The threshold detector circuit 44 shown in FIG. 4 can utilize an operational amplifier, such as a National TL074, a diode, such as a 1N914A, and a transistor, such as a 2N3904. The threshold detector circuit 44 detects when the signal generated by the impact force exceeds a predetermined threshold level. This is important in isolating weak signals that may be generated by vibrations and the like experienced by the apparatus.

The signals received by threshold detector circuit 44 that meet or exceed the predetermined threshold level are applied to a timer and logic circuit 48 and a reflex tester circuit 56.

The timer and logic circuit 48 shown can utilize timers such as Motorola MC14538s. When a signal exceeding the predetermined threshold level is received by the timer and logic circuit 48, the timer and logic circuit 48 generates a reset signal. Additionally, after approximately three seconds, if a signal has not exceeded the predetermined threshold level, a reset signal is generated to clear the previous measurement.

The reset signal generated by the timer and logic circuit 48 is applied to a peak detector and storage circuit 46. The peak detector and storage circuit 46 can utilize operational amplifiers, such as a National TL074s, a diode, such as a 1N914A and a capacitor such as a tantalum type. The reset signal received from the timer and logic circuit 48 operates to reset the peak detector and storage circuit 46. After being reset, the peak detector and storage circuit 46 tracks the signal generated by the impact force and stores the peak value of the signal.

The signal tracked and stored in the peak detector and storage circuit 46 is applied to a display circuit 50 which can include an analog-to-digital convertor, such as a Harris ICL7136. The digital output of the analog-to-digital convertor is then applied to a digital display, such as a Varitronix VI-302 liquid crystal display, which provides the user with an indication of the impact force of his or her punches and/or kicks. The display circuit 50 can also be configured to provide an audio indication of the impact force if desired as well as other indications. Such display circuitry are well known in the art.

The electrical circuit 38 and the pressure sensor 36 shown in FIG. 4 are powered by a battery 52 which is connected to a battery control circuit 54. The battery control circuit 54 provides a battery saving time-out which will turn the circuit off after a predetermined time interval has passed since the last detected impact.

Figure 5:
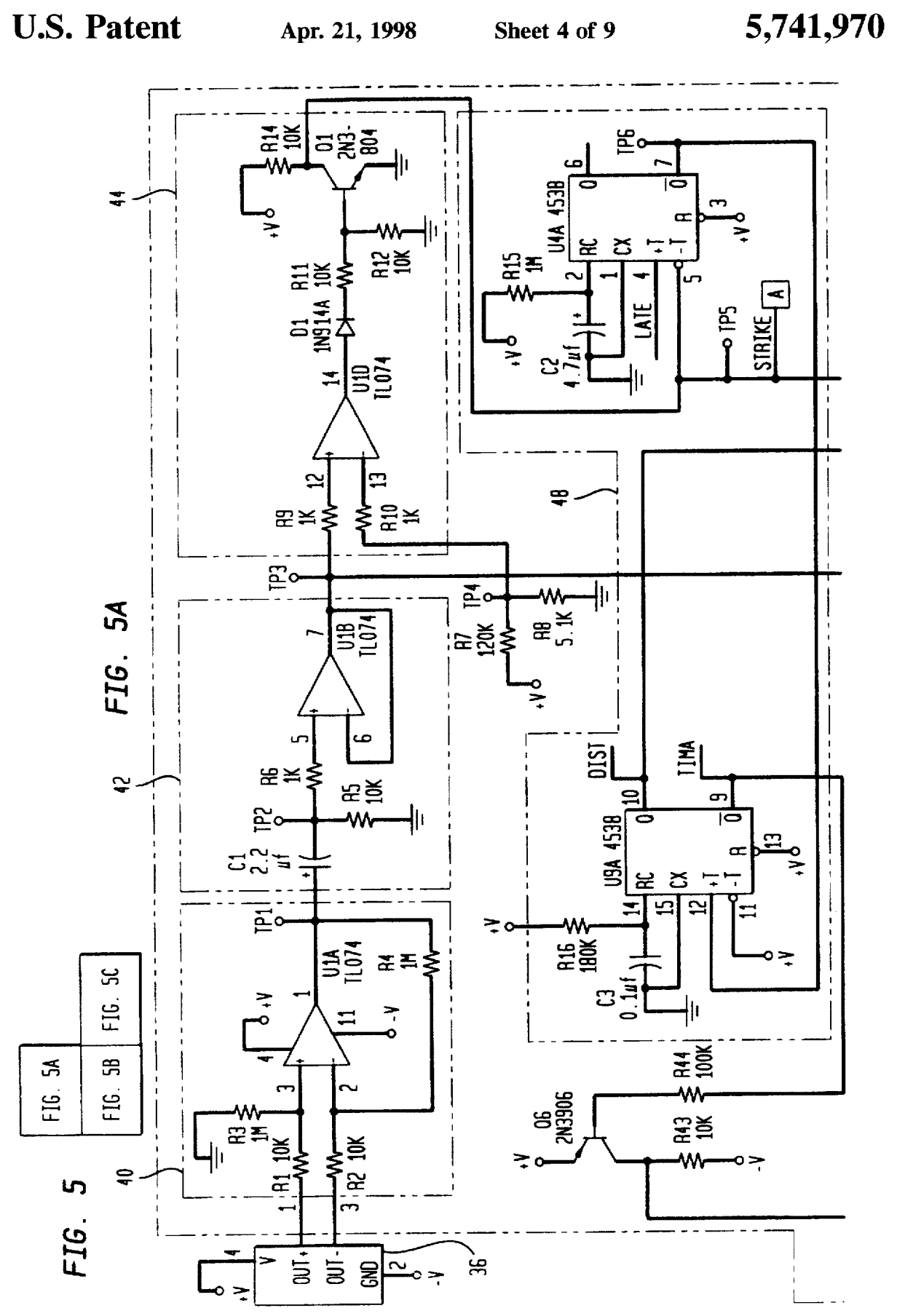
Figure 5B:
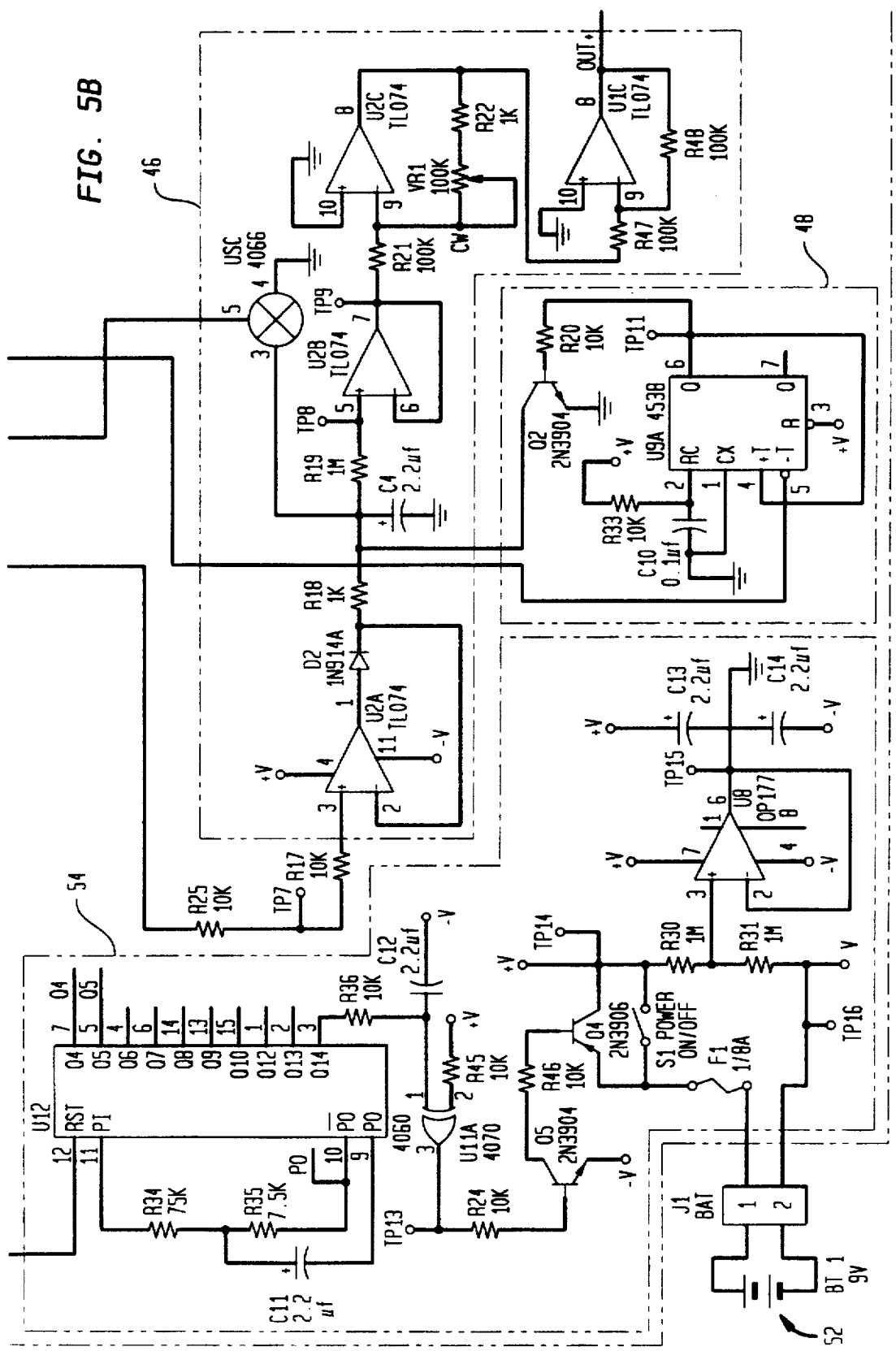
FIG. 5 is a schematic diagram of an implementation of the electrical circuit of the present invention.
Figure 5C:
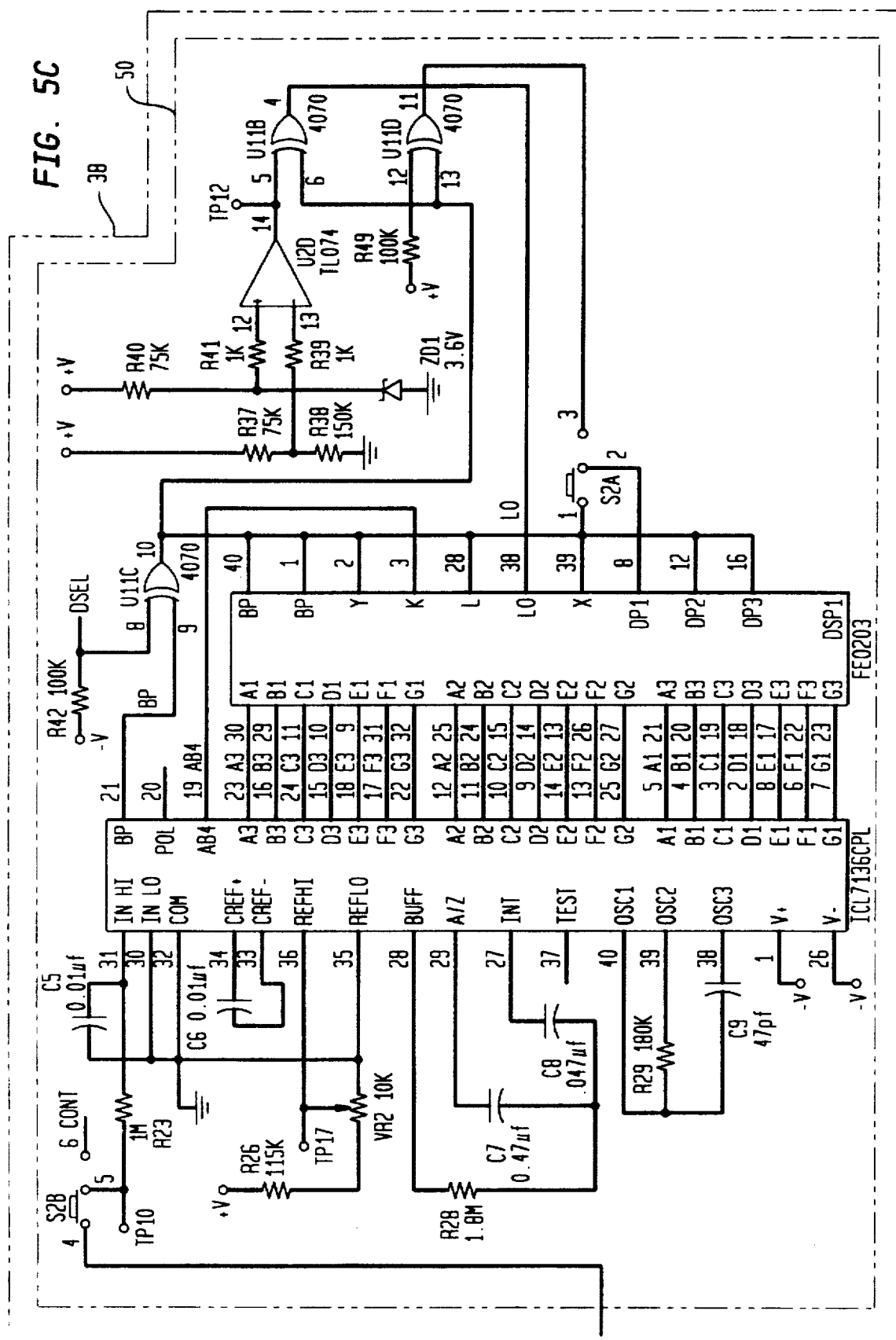

Referring to FIG. 5, there is shown a schematic of one practical implementation of the electrical circuit 38 which is coupled to the pressor transducer 36 of the present invention. The elements of the block diagram used in FIG. 4 are identified in the schematic of FIG. 5 with similar numbers. The electrical circuit 38 of the present invention is constructed from individual electronic components elements that are well known in the art. As such, these components can be selected from readily available commercial sources.

Figure 6:
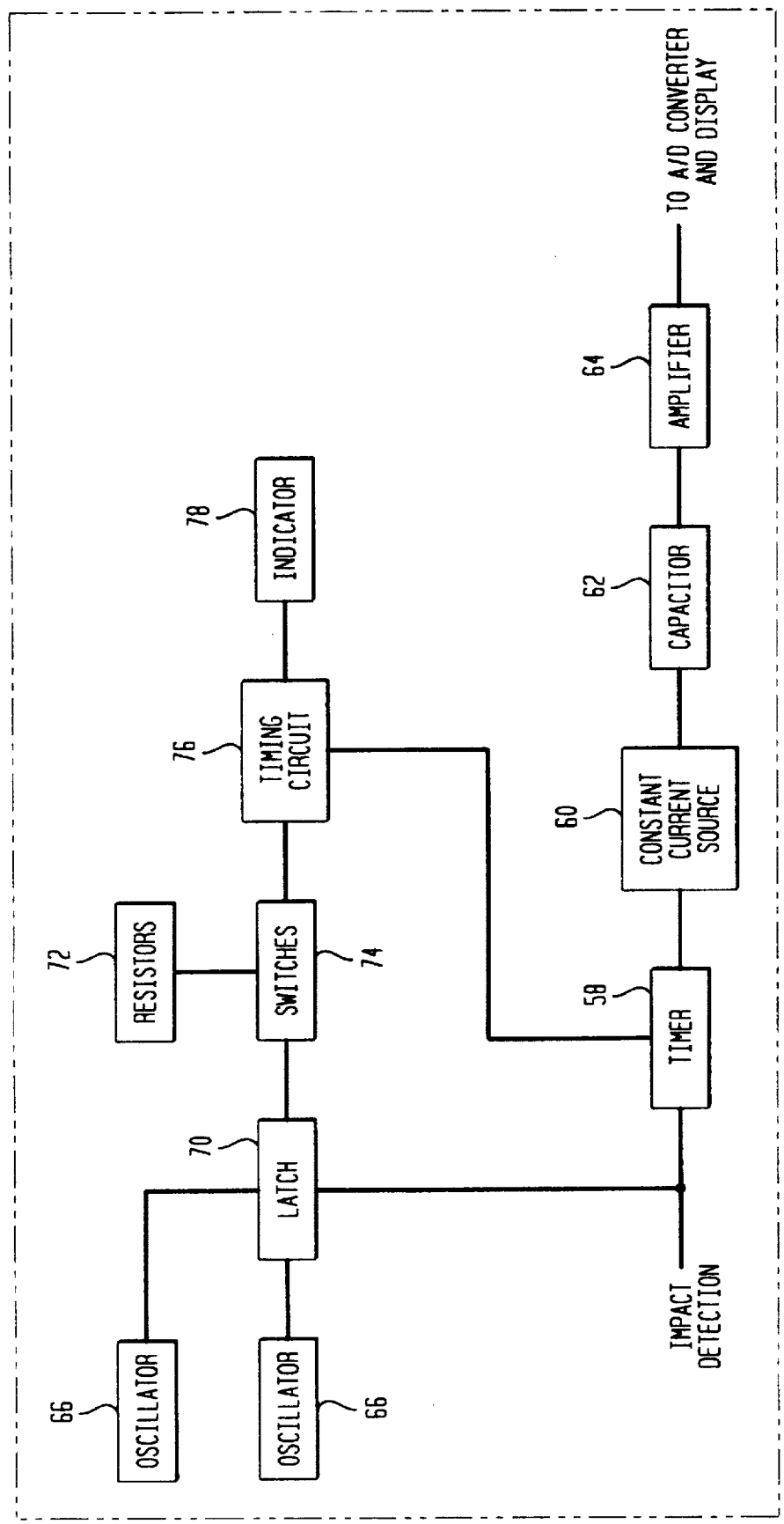
FIG. 6 is a block diagram of the reflex testing circuit of the present invention.

Referring to FIG. 6, there is shown a block diagram of the reflex tester circuit 56 mentioned earlier. As earlier stated, the signals received by threshold detector circuit 44 that meet or exceed the predetermined threshold level are applied to the reflex tester circuit 56. The reflex tester circuit 56 measures the time it takes the user to respond to a signal and strike the impact apparatus 10. This feature is very useful in testing and conditioning the reflexes of the user.

A switch 57, such as a slide switch or the like, is used to enable the operator to display either the reflex time (reflex mode) or the impact force (impact mode) since the reflex tester circuit 56 operates in conjunction with the previously described impact measurement circuitry. When the user selects the reflex mode, other display functions such as decimal points and the like are selected and the response time signal generated by the reflex tester circuit 56 is coupled to the display circuit 50 so that the display shows response time.

At the beginning of a timing cycle, an auditory indicator 78, such as a piezoelectric type buzzer or other like indicator is sounded when it receives a signal from a timing circuit 76 coupled thereto. It should be understood, that any suitable visual indicator can be used if desired. In any case, the user must immediately respond by striking the impact apparatus 10 as quickly as possible. At the same time the indicator 78 is activated, the timing circuit 76 applies a signal to a timer 58. The timer 58 applies a signal to a constant current source 60 which charges a capacitor 62. The capacitor 62 is charged in a linear fashion so that the voltage level on the capacitor 62 gives an instantaneous indication of how long the capacitor 62 has been charged. In the preferred embodiment, the constant current source is made up of an operational amplifier and resistors. The capacitor 62 can be a tantalum type capacitor.

When a strike is detected, the charging immediately stops, so that the voltage across the capacitor 62 now shows how much time has passed since the indicator 78 has sounded. The voltage across the capacitor is coupled to the previously described display circuit 50 through an isolation amplifier 64. The value of the voltage is held for a short period of time before the capacitor is discharged, and a new cycle begins.

In order to prevent the user from becoming accustomed to a constant signal repetition rate, the reflex testing circuit includes two independent free-running oscillators 66 which randomly change the timing of the circuit. A latch 70 interfaces the oscillators 66 with analog switches 74. The analog switches 74 select the appropriate resistors for the timing circuit 76. This arrangement allows the time which passes between the cycles to be randomly varied.

In the event that a punch or kick hasn't been detected in a predetermined amount of time, the system resets itself, and a new cycle begins.

Figure 7A:
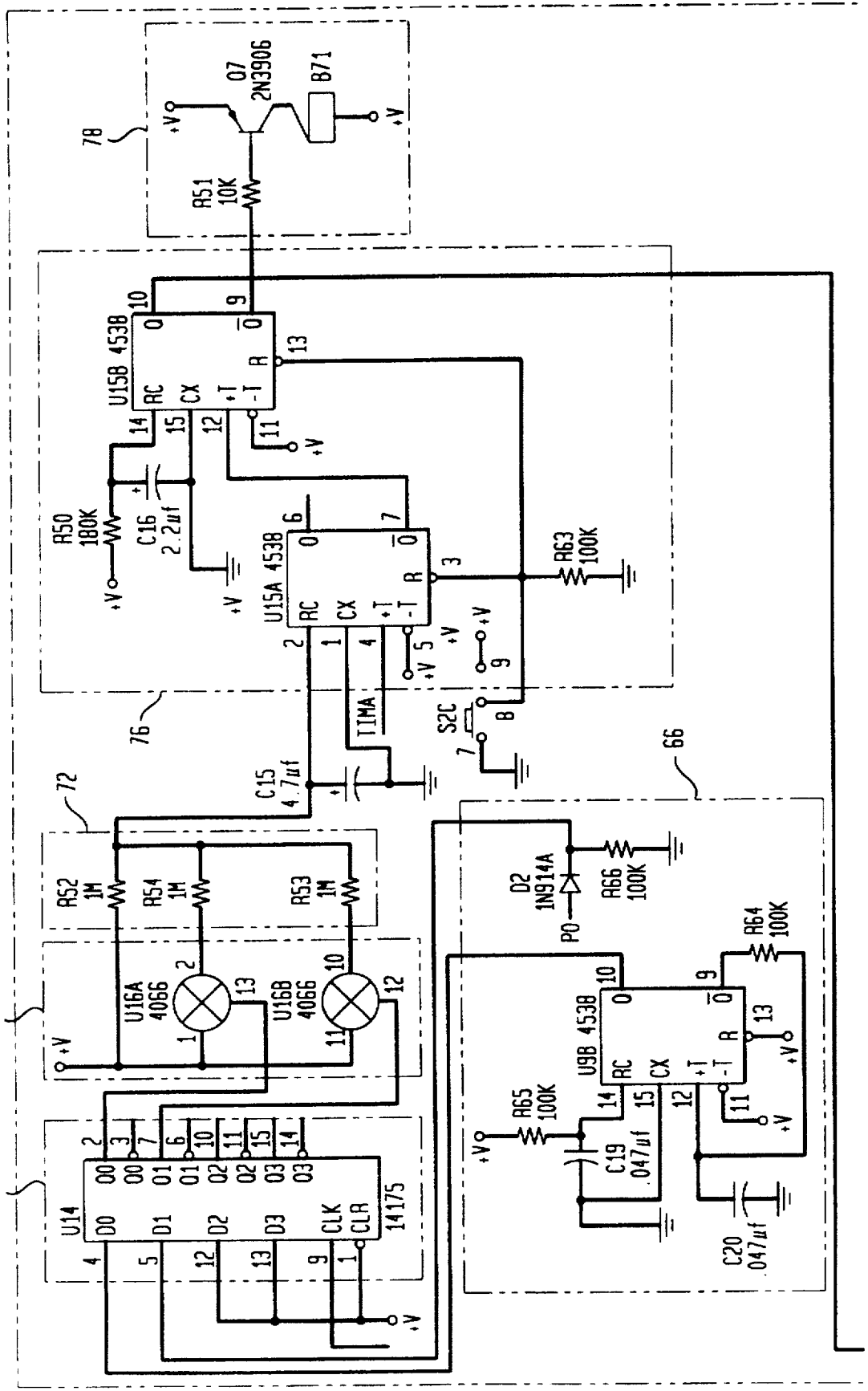
FIG. 7 is a schematic diagram of an implementation of the reflex testing circuit of the present invention.

Referring to FIG. 7, there is shown a schematic of one practical implementation of the flex testing circuit 56 described above. The elements of the block diagram used in FIG. 6 are identified in the schematic of FIG. 7 with similar numbers. As with the electrical circuit 38 of the present invention, the reflex testing circuit 56 is constructed from individual electronic components elements that are well known in the art. As such, these components can be selected from readily available commercial sources. Alternatively, a microprocessor could be employed to perform the above described functions if desired.

It should be understood that the embodiment shown and described herein is merely exemplary and that a person skilled in the art may make many variations and modifications to this embodiment utilizing functionally equivalent elements to those shown and described herein. For example, the electrical circuit described above is one of many possible circuits which can be employed such that only impacts delivered by the user which cause a rate of change in pressure meeting a given threshold value are displayed. In particular, other embodiments of the electrical circuit can utilize devices such as a microcomputer to process the signals generated by the pressure sensor 36. In such an embodiment, the microcomputer could be used to record multiple impacts delivered by the user and track trends for subsequent display and printing.

Accordingly, any and all such variations or modifications as well as others which may become apparent to those skilled in the art, are intended to be included within the scope of the invention as defined by the appended claims.

I claim:

1. An apparatus for measuring impacts delivered by a user, comprising:
   impact receiving means for absorbing an impact delivered by the user and generating a pressure pulse in response to the impact delivered on said impact receiving means by the user; and signaling means communicating with said impact receiving means for receiving the pressure pulse generated by said impact receiving means and providing an electrical signal which is indicative of the force and speed of the impact delivered by the user;

wherein said impact receiving means includes a layer of resilient open cell material for generating the pressure pulse, a layer of fibrous material for guiding the pressure pulse toward said signaling means and a layer of resilient closed cell material for reflecting said pressure pulse if received from said layer of resilient open cell material, said layer of fibrous material being oriented between said layer of resilient open cell material and said layer of resilient closed cell material, wherein said layer of fibrous material and said layer of resilient closed cell material coact to vary the amplitude of the pressure pulse generated in said layer of resilient open cell material according to the location where the impact is received on said impact receiving means by the user.

2. The apparatus according to claim 1, wherein said signaling means comprise sensor means.

3. The apparatus according to claim 2, further comprises:

signal processing means coupled to said pressure sensor means for processing said electrical signal into a measure of impact force and the time it takes the user to respond to an indicator and strike said apparatus; and display means for displaying said measure of impact force and said response time, wherein said apparatus reacts only to an impact delivered by the user which causes a rate of change in pressure meeting a given threshold value.

4. The apparatus according to claim 3, further comprising means for informing the user when a preset level of impact force has been reached.

5. The apparatus according to claim 3, further comprising means for recording multiple impacts delivered by the user.

6. An apparatus for measuring the force of an impact delivered by a user, comprising:

impact receiving means for absorbing an impact delivered by the user and generating a pressure pulse in response to the impact delivered on said impact receiving means by the user, said impact receiving means including a desired target point; and signaling means for receiving the pressure pulse generated by said impact receiving means and providing an electrical signal which is indicative of the impact delivered by the user; and port means extending between said impact receiving means and said signaling means for directing said pressure pulse generated by said impact receiving means toward said signaling means, said port means being located adjacent to said desired target point so that the amplitude of a pressure pulse generated by an impact delivered a distance away from said target point is attenuated proportionately to said distance away from said target area;

wherein said impact receiving means includes a layer of resilient, randomly arranged open cell material for generating the pressure pulse, a layer of fibrous material for guiding the pressure pulse toward said signaling means and a layer of resilient closed cell material for reflecting said pressure pulse if received from said layer of resilient open cell material, said layer of fibrous material being oriented between said layer of resilient open cell material and said layer of resilient closed cell material, wherein said layer of fibrous material and said layer of resilient closed cell material coact to vary the amplitude of the pressure pulse generated in said layer of resilient open cell material according to the location where the impact is received on said impact receiving means by the user.

7. The apparatus according to claim 6, wherein said port means extends through said layer of resilient closed cell material.

8. The apparatus according to claim 6, wherein signaling means and said signal processing means are separated from said impact receiving means by a solid member which forms one portion of an enclosure which encases said signaling means and said signal processing means.

9. The apparatus according to claim 6, wherein said signaling means comprises pressure sensor means.

10. The apparatus according to claim 9, further comprises:

signal processing means coupled to said pressure sensor means for processing said electrical signal into a measure of impact force and the time it takes the user to respond to an indicator and strike said apparatus;

display means for displaying said measure of impact force and said response time;

means for informing the user when a preset, level of impact force has been reached; and means for recording multiple impacts delivered by the user, wherein said apparatus reacts only to impacts delivered by the user which cause a rate of change in pressure meeting a given threshold value.

11. An apparatus for measuring impacts delivered by a user, comprising:

impact receiving means for absorbing an impact delivered by the user and generating a pressure pulse in response thereto;

signaling means communicating with said impact receiving means, for receiving the pressure pulse generated by said impact receiving means and providing an electrical signal which is indicative of the impact;

high pass filter means coupled to said signaling means, for filtering said electrical signal;

detector means coupled to said high pass filter means, for detecting if said electrical signal exceeds a predetermined level;

track/storage means responsive to said detector means and coupled to said high pass filter means, for tracking a peak level of an electrical signal exceeding said predetermined level and storing said peak level;

reflex tester means coupled to and responsive to said detector means, for measuring the time it takes for the user to respond to an indicator signal and impact said apparatus; and display means selectively coupled to said track/storage means and said reflex tester means, for displaying said peak level as a measure of force and for displaying said time for responding to said indicator signal.

12. The apparatus according to claim 11, wherein said display means comprises an analog to digital converter coupled to a digital display.

* * * * *